US008889366B2

(12) United States Patent
Struck et al.

(10) Patent No.: US 8,889,366 B2
(45) Date of Patent: Nov. 18, 2014

(54) MARKER FOR GRAFT FAILURE AND MORTALITY

(75) Inventors: Joachim Struck, Berlin (DE); Stephanus Johannes Bakker, Groningen (NL)

(73) Assignee: B.R.A.H.M.S. GmbH, Henningsdorf (DE)

( * ) Notice: Subject to any disclaimer, the term of this patent is extended or adjusted under 35 U.S.C. 154(b) by 996 days.

(21) Appl. No.: 12/995,772

(22) PCT Filed: May 29, 2009

(86) PCT No.: PCT/EP2009/056625
§ 371 (c)(1),
(2), (4) Date: Mar. 18, 2011

(87) PCT Pub. No.: WO2009/147096
PCT Pub. Date: Dec. 10, 2009

(65) Prior Publication Data
US 2011/0171750 A1 Jul. 14, 2011

(30) Foreign Application Priority Data
Jun. 4, 2008 (EP) .................................... 08157595

(51) Int. Cl.
*G01N 33/53* (2006.01)
*G01N 31/00* (2006.01)
*G01N 33/74* (2006.01)
*G01N 33/68* (2006.01)

(52) U.S. Cl.
CPC ............ *G01N 33/6893* (2013.01); *G01N 33/74* (2013.01); *G01N 2333/585* (2013.01); *G01N 2800/245* (2013.01)
USPC ........... 435/7.21; 435/7.1; 436/501; 436/518; 424/9.1; 424/520; 422/430; 530/300; 530/350

(58) Field of Classification Search
CPC ........... G01N 33/6893; G01N 2800/52; A61K 2300/00; G06Q 50/22
See application file for complete search history.

(56) References Cited

PUBLICATIONS

Oczenski et al. (European Journal of Anaesthesiology, Issue 2, Mar. 1998, pp. 202-209).*
International Search Report of PCT/EP2009/056625, Date of Completion Sep. 29, 2009, Date of Mailing Oct. 15, 2010.

Fazakas J et al: "Analysis of systemic and regional procalcitonin serum levels during liver transplantation," Transplant International 20030701 DE, vol. 16, No. 7, Jul. 1, 2003, pp. 465-470, XP008093852 ISSN: 0934-0874.
Morgenthaler Nils G et: "Detection of procalcitonin (PCT) in healthy controls and patients with local infection by a sensitive ILMA", Clinical Laboratory, CLN Lab Publications, Heildelberg, vol. 48, No. 5-6, Jan. 1, 2002, pp. 263-270, XP009072951, ISSN: 1433-6510.
Qedra N et al: "Procalcitonin and modified SOFA score: The best predictors of mortality after heart and lung transplantation." Journal of Heart and Lung Transplantation, vol. 23, No. 2S, Feb. 2004, pp. S117, XP008093870 & Twenty-Fourth Annual Meeting and Scientific Sessions of the InternationalSociety for Heart and Lung; San Francisco, CA, USA; Apr. 21-24, 2007 ISSN: 1053-2498 abstract.
Dornbusch H J et al: "Non-infectious causes of elevated procalcitonin serum levels in pediatric patents with hematologic and oncologic disorders." Abstracts of the Interscience Conference on Antimicrobial Agents and Chemotherapy, vol. 42, 2002, p. 135, XP008093859 & American Society for Microbiology (ASM) Annual Meeting on Infectious Disaease; San Diego, CA, USA; Sep. 27-30, 2002 abstract.
Pihusch Markus et al: "Evaluation of C-reactive rotein inteleukin-6, and procalcitonin levels in allogeneic hematopoietic stem cell recipients" European Journal of Haematology, vol. 76, No. 2 Feb. 2006, pp. 93-101, XP008093872 ISSN: 0902-4441 abstract.
Eberhard O K et al: "Procalcitonin in the early phase after renal transplantation—Will it add to diagnostic accuracy?" Clinical Transplantation DK, vol. 12, No. 3, Jun. 1998, pp. 206-211, XP008093851, ISSN: 0902-0063 abstract.
Jung D-Y et al: "Combined use of myeloid-related protein 8/14 and procalcitonin as diagnostic markers for acute allograft rejection in kidney transplantation recipients" Tansplant Immunology NL, vol. 18, No. 4, Feb. 2008, pp. 338-343, XP008093862.
Jaresova M et al: "Serum procalcitonin concentrations in transplant patients with acute rejection and bacterial infections" Immunology Letters, vol. 69, No. 3, Sep. 1, 1999, pp. 355-358, XP002488639, ISSN: 0165-2478 abstract.
Kozio L et al: "Procalcintonin (PCT) and C-reactive protein (CRP) serum levels in cadaver kidney recipients" Nephrology Dialysis Transplantation, Oxford University Press, GB, vol. 16, No. 6, Jun. 1, 2001, p. A216, XP008093865, ISSN: 0931-0509.
Striz I et al: "MRP 8/14 and procalcitonin serum levels in organ transplantations." Annals of Transplantation: Quarterly of the Polish Transplantation Society 2001, vol. 6, No. 2, 2001, pp. 6-9 XP008093861 ISSN: 1425-9524.

* cited by examiner

*Primary Examiner* — Lisa Cook
(74) *Attorney, Agent, or Firm* — Millen, White, Zelano, Branigan, P.C.

(57) ABSTRACT

Subject of the present invention is a biomarker for graft failure and/or mortality after organ transplantation. Procalcitonin was found to be a useful marker for the prediction or risk stratification for graft failure and/or mortality of a subject who has received an organ transplant and monitoring and therapy guidance of such subject.

22 Claims, 4 Drawing Sheets

MARKER FOR GRAFT FAILURE AND MORTALITY

FIELD OF THE INVENTION

Subject of the present invention is a biomarker for graft failure and/or mortality after organ transplantation. Procalcitonin (PCT) was found to be a useful marker for the prediction or risk stratification for graft failure and/or mortality of a subject who has received an organ transplant and monitoring and therapy guidance of such subject.

BACKGROUND OF THE INVENTION

Chronic transplant dysfunction (CTD) after renal transplantation is characterized by renal function decline and proteinuria.

One-year graft survival after renal transplantation has steadily improved from approximately 40% in the 1970's to more than 90% nowadays (Merville P. Combating chronic renal allograft dysfunction: optimal immunosuppressive regimens. Drugs 2005; 65(5):615-631; http://www.unos.org 2008, RefType: Generic). Long-term graft survival, however, has not paralleled this improvement. Approximately half of all cadaveric renal allografts are lost within 10-12 years after transplantation (Hariharan S, Johnson C, Bresnahan B, Taranto S, McIntosh M, Stablein D. Improved Graft Survival after Renal Transplantation in the United States, 1988 to 1996. N Engl J Med 2000; 342(9):605-612). One leading cause is late allograft failure in association with chronic transplant dysfunction (CTD) (Kreis H A, Ponticelli C. Causes of late renal allograft loss, chronic allograft dysfunction, death, and other factors. Transplantation 2001; 71(11 Suppl): SS5-SS9). Currently, there are no good biomarkers to predict the development of CTD (Marsden P A. Predicting outcomes after renal transplantation-new tools and old tools. N Engl J Med 2003; 349(2):182-184).

There is an emerging notion in the renal transplant community that the pathogenesis of CTD includes inflammation (Kreis H A, Ponticelli C. Causes of late renal allograft loss: chronic allograft dysfunction, death, and other factors. Transplantation 2001; 71(11 Suppl):SS5-SS9; Vazquez M A, Jeyarajah D R, Kielar M L, Lu C Y. Long-term outcomes of renal transplantation: a result of the original endowment of the donor kidney and the inflammatory response to both alloantigens and injury. Curr Opin Nephrol Hypertens 2000; 9(6):643-648). Procalcitonin (PCT) has been suggested as a biomarker for bacterial infections and sepsis (Assicot M, Gendrel D, Carsin H, Raymond J, Guilbaud J, Bohuon C. High serum procalcitonin concentrations in patients with sepsis and infection. Lancet 1993; 341(8844):515-518; Becker K L, Nylen E S, White J C, Muller B, Snider R H, Jr. Clinical review 167: Procalcitonin and the calcitonin gene family of peptides in inflammation, infection, and sepsis: a journey from calcitonin back to its precursors. J Clin Endocrinol Metab 2004; 89(4):1512-1525). Recently, it has been found that parenchymal cells stimulated by activated macrophages in infected tissues rather than peripheral blood mononuclear cells underlie very high concentrations of circulating PCT during sepsis (Linscheid P, Seboek D, Schaer D J, Zulewski H, Keller U, Muller B. Expression and secretion of procalcitonin and calcitonin gene-related peptide by adherent monocytes and by macrophage-activated adipocytes. Crit Care Med 2004; 32(8):1715-1721). Animal and human studies have now shown that in sepsis, parenchymal cells (including kidney, liver, lung, muscle and adipocytes) are the principal source of circulating PCT (Linscheid P, Seboek D, Schaer D J, Zulewski H, Keller U, Muller B. Expression and secretion of procalcitonin and calcitonin gene-related peptide by adherent monocytes and by macrophage-activated adipocytes. Crit Care Med 2004; 32(8):1715-1721; Linscheid P, Seboek D, Nylen E S et al. In vitro and in vivo calcitonin I gene expression in parenchymal cells: a novel product of human adipose tissue. Endocrinology 2003; 144(12):5578-5584; Muller B, White J C, Nylen E S, Snider R H, Becker K L, Habener J R Ubiquitous expression of the calcitonin-i gene in multiple tissues in response to sepsis. J Clin Endocrinol Metab 2001; 86(4396-404).

It was surprisingly found that PCT is an independent predictor for late graft failure and/or mortality. Is is, therefore, a promising new biomarker for the prediction of graft loss (GL) and/or mortality.

DESCRIPTION OF THE INVENTION

Subject of the present invention is a method for the prediction or risk stratification for graft failure and/or mortality of a subject who has received an organ transplant and monitoring and therapy guidance of such subject comprising the determination of procalcitonin or fragments thereof with at least 12 amino acids in a sample taken from said subject.

In a preferred embodiment, the invention relates to a method for the prediction or risk stratification for graft failure and/or mortality of a subject that has received an organ transplant and monitoring and therapy guidance of such a subject, comprising the determination of procalcitonin or fragments thereof with at least 12 amino acids in a sample taken from said subject, wherein the level of procalcitonin associated with an increased risk for graft failure and/or mortality is above a cut-off, which is below 0.1 ng/mL, preferably below 0.08 ng/mL, more preferably below 0.05 ng/mL and most preferably below 0.025 ng/mL.

Thus, the method of the present invention employs a sensitive assay to detect low concentrations of procalcitonin which enables the use of low indicative threshold levels.

In the context of the present invention, the term "risk stratification" denotes an assignment of a probability to experience certain adverse events to an individual. Hereby, the individual may preferably be accounted to a certain risk category, wherein categories comprise for instance high risk versus low risk, or risk categories based on numeral values, such as risk category 1, 2, 3, etc.

As mentioned herein in the context of PCT, the term "fragment" refers to smaller peptides derivable from PCT, which hence comprise a partial sequence of PCT. Said fragments are derivable from PCT by saponification of one or more of its peptide bonds.

In a preferred embodiment of the present invention the subject has received a renal transplant. Thus, subject of the present invention is a method for the prediction or risk stratification for graft failure and/or mortality of a subject who has received an renal transplant and monitoring and therapy guidance of such subject comprising the determination of procalcitonin or fragments thereof with at least 12 amino acids in a sample taken from said subject.

In another preferred embodiment the subject is not under a condition selected from the group comprising: infection or escalated forms of infection like sepsis, severe sepsis or septic shock. This means that the subject is not under a condition requiring antimicrobial treatment.

In a preferred embodiment of the invention the subject's level of procalcitonin is not influenced anymore by the surgical trauma caused by the organ transplantation. It is known that subjects that underwent major surgery have an elevated PCT level for some days. Thus, in a preferred embodiment a sample is taken from the subject who has received an organ transplant, at least after half a day after surgery, preferably at least after one day, more preferably at least after two days, even more preferably at least after three days, even more preferably at least after four days, even more preferably at least after five days, even more preferably at least after six days, even more preferably at least after one week. Thus, according to the method of the invention the sample is preferably taken from the subject not earlier than one week after transplantation, preferably one month or later after transplantation. In a special embodiment the sample may be taken one year after transplantation or later.

According to the present invention said sample is selected from a group comprising a plasma sample, a serum sample, a blood sample or fractions thereof, a lymphatic fluid sample, a urine sample or an extract of any of the aforementioned samples.

The method according to the present invention is a method for prediction of long term graft failure, whereby long term means a period of more than one year, preferably up to 5 years. The method according to the present invention is also a method for prediction of short term graft failure, whereby short term means a period of one week up to one year.

The present invention also comprises a method for prediction of intermediate or long term graft failure, whereby long term means a period of more than one year, preferably up to 5 years and intermediate term means a period of between 2 months and 1 year, e.g. 2, 3, 4, 5, 6, 7, 8, 9, 10, 11 or 12 months after transplantation.

In a preferred embodiment of the method according to the present invention the level of procalcitonin may preferably be correlated with the prediction or risk stratification for graft failure and/or mortality by a method which may be selected from the following alternatives:
  correlation with respect to the median of the level of procalcitonin in an ensemble of pre-determined samples,
  correlation with respect to quantiles (e.g. tertiles) of the level of procalcitonin in an ensemble of pre-determined samples, and
  correlation with a mathematical model, such as for example Cox Regression.

A person skilled in the art will understand that this is not an exhausting listing of methods. The person skilled in the art may know further methods.

According to the present invention the level of procalcitonin associated with an increased risk for graft failure and/or mortality is above the median level of the normal population. The median level of the normal population has been determined previously to be 0.0127 ng/mL (Morgenthaler N G, Struck J, Fischer-Schulz C, Seidel-Mueller E, Beier W, Bergmann A. Detection of procalcitonin (PCT) in healthy controls and patients with local infection by a sensitive ILMA. Clin Lab. 2002, 48(5-6):263-70.)

Preferably, the level of procalcitonin associated with an increased risk for graft failure and/or mortality is above the median of the normal population (0.0127 ng/mL) but below 0.1 ng/mL, preferably below 0.08 ng/mL, more preferably below 0.05 ng/mL, most preferably below 0.025 ng/mL. This means, that the preferred cut-off value above which the level of procalcitonin in the sample of a patient is indicative for an increased risk for graft failure and/or mortality in the patient is below 0.1 ng/mL, preferably below 0.08 ng/mL, more preferably below 0.05 ng/mL, most preferably below 0.025 ng/mL but above the median of the normal population (0.0127 ng/mL). Procalcitonin concentrations above 0.1 ng/mL or 0.25 ng/mL are used as cut-off to diagnose bacterial infections, which require antibiotic treatment (Christ-Crain M, Jaccard-Stolz D, Bingisser R, Gencay M M, Huber P R, Tamm M, Müller B. Effect of procalcitonin-guided treatment on antibiotic use and outcome in lower respiratory tract infections: cluster-randomised, single-blinded intervention trial. Lancet 2004 Feb. 21; 363(9409):600-7.) A suitable cut-off value as determined by ROC analysis optimizing sensitivity and specificity for the prediction of an increased risk for graft failure is 0.029 ng/mL and for mortality is 0.028 ng/mL (table 4). The person skilled in the art knows that the precise cut-off value depends on several factors. Thus, the person skilled in the art knows how to precisely define a single cut-off concentration for procalcitonin, above which concentrations are associated with such an increased risk, since cut-off values depend on the calibration of the test and the type of mathematical model used to describe such association; i.e. if the target population is divided according to the procalcitonon concentration in two subgroups of identical size, the resulting median level might represent a useful cut-off; alternatively the same population might be divided in three subgroups of identical size, and the procalcitonin concentration separating the highest from the middle tertile might represent a useful cut-off value, which is different, however, from the cut-off value representing the median level of the population. Other mathematical models might come up with other useful cut-off concentrations of procalcitonin.

In a preferred embodiment of the method of the present invention the level of one or more further markers or clinical parameter, which is associated with an increased risk for graft failure and/or mortality, is additionally determined and used.

In a preferred embodiment said one or more clinical parameters are selected from group comprising: age, gender, prior history of diseases, in particular diabetes, body mass index, genetic predisposition/family history, ethnic background, habits which affect said propensity, such as smoking, alcohol consumption, diet.

In a preferred embodiment said one or more further markers are selected from the group comprising: markers for renal function, inflammation markers and markers associated with the cardiovascular and osmotic regulation.

In a preferred embodiment said marker for renal function is selected from the group comprising creatinine clearance, proteinuria and lipid markers. Lipid markers may be HDL and/or triglycerides.

In a preferred embodiment said inflammation marker is C-reactive protein.

In a preferred embodiment said marker associated with the cardiovascular and osmotic regulation is selected from a group comprising proBNP or fragments thereof of at least 12 amino acids including BNP and NT-proBNP, proANP or fragments thereof of at least 12 amino acids including NT-proANP and MR-proANP, proAdrenomedullin or fragments thereof of at least 12 amino acids including Adrenomedullin, PAMP and MR-proADM, proEndothelin or fragments thereof of at least 12 amino acids including Endothelin-1, big-Endothelin-1, CT-proET-1 and NT-proET-1, proVasopressin or fragments thereof of at least 8 amino acids including Vasopressin, Copeptin and Neurophysin 2.

Subject of the present invention is one embodiment a method comprising the steps:
  taking a sample from a subject after renal transplantation,
  determining the level of procalcitonin or fragments thereof with at least 12 amino acids in a sample taken from said subject, and
  correlating the level of procalcitonin or fragments thereof with at least 12 amino acids with a prognosis.

In a preferred embodiment of the method according to the present invention the level of procalcitonin or fragments thereof with at least 12 amino acids is determined with a diagnostic assay.

In a preferred embodiment the steady-state circulating PCT-concentration is determined.

The diagnostic assay used in the context of the present invention can be of any type applied in the field of diagnostics, including but not restricted to assay methods based on enzymatic reactions, luminescence, in particular fluorescence or radio chemicals. The preferred detection methods comprise rapid test formats including immunochromatography, radio-immunoassays, chemiluminescence- and fluorescence-immunoassays, immunoblot assays, enzyme-linked immunoassays (ELISA), luminex-based bead arrays, and protein microarray assays. The assay types can further be microtitre plate-based, chip-based, bead-based, wherein the biomarker proteins can be attached to the surface or in solution. The assays can be homogenous or heterogeneous assays, sandwich assays, competitive and non-competive assays (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134).

In the context of the present invention, capture molecules used in a diagnostic assay may be selected from the group comprising a nucleic acid molecule, a carbohydrate molecule, a PNA molecule, a protein, an antibody, a peptide or a glycoprotein. Preferably, the capture molecules are antibodies, including fragments thereof with sufficient specificity to a target, and including recombinant antibodies, as well as chemically and/or biochemically modified derivatives of said antibodies or fragments derived from the variant chain with a length of at least 12 amino acids thereof.

According to an especially preferred embodiment the diagnostic assay for procalcitonin or fragments thereof with at least 12 amino acids is ultrasensitive and has a functional assay sensitivity (defined as the smallest concentration which can be determined with a maximal interassay coefficient of variation (CV) of 20%) below 0.1 ng/mL, preferably below 0.08 ng/mL, more preferably below 0.05 ng/mL, most preferably below 0.025 ng/mL.

Subject of the invention is further the use of measurement of procalcitonin or fragments thereof with at least 12 amino acids for the prediction of risk stratification for graft failure and/or mortality of a subject who has received an organ transplant and monitoring and therapy guidance of such subject.

Subject of the invention is further the use of an immunoassay having an assay sensitivity (defined as the smallest concentration which can be determined with a maximal interassay CV of 20%) below 0.1 ng/mL, more preferably below 0.05 ng/mL, most preferably below 0.025 ng/mL, for the prediction or risk stratification for graft failure and/or mortality of a subject who has received an organ transplant and monitoring and therapy guidance of such subject.

As used herein, terms such as "marker" "prognostic marker" or "biomarker" or "biological marker" are used interchangeably and relate to measurable and quantifiable biological parameters (e.g., specific enzyme concentration, specific hormone concentration, specific gene phenotype distribution in a population, presence of biological substances) which serve as indices for health- and physiology-related assessments, such as disease risk, psychiatric disorders, environmental exposure and its effects, disease diagnosis, metabolic processes, substance abuse, pregnancy, cell line development, epidemiologic studies, etc. Furthermore, a biomarker is defined as a characteristic that is objectively measured and evaluated as an indicator of normal biological processes, pathogenic processes, or pharmacologic responses to a therapeutic intervention. A biomarker may be measured on a biosample (as a blood, urine, or tissue test), it may be a recording obtained from a person (blood pressure, ECG, or Holter), or it may be an imaging test (echocardiogram or CT scan) (Vasan et al. 2006, Circulation 113:2335-2362).

Biomarkers can indicate a variety of health or disease characteristics, including the level or type of exposure to an environmental factor, genetic susceptibility, genetic responses to exposures, biomarkers of subclinical or clinical disease, or indicators of response to therapy. Thus, a simplistic way to think of biomarkers is as indicators of disease trait (risk factor or risk biomarker), disease state (preclinical or clinical), or disease rate (progression). Accordingly, biomarkers can be classified as antecedent biomarkers (identifying the risk of developing an illness), screening biomarkers (screening for subclinical disease), diagnostic biomarkers (recognizing overt disease), staging biomarkers (categorizing disease severity), or prognostic biomarkers (predicting future disease course, including recurrence and response to therapy, and monitoring efficacy of therapy). Biomarkers may also serve as surrogate end points. A surrogate end point is one that can be used as an outcome in clinical trials to evaluate safety and effectiveness of therapies in lieu of measurement of the true outcome of interest. The underlying principle is that alterations in the surrogate end point track closely with changes in the outcome of interest. Surrogate end points have the advantage that they may be gathered in a shorter time frame and with less expense than end points such as morbidity and mortality, which require large clinical trials for evaluation. Additional values of surrogate end points include the fact that they are closer to the exposure/intervention of interest and may be easier to relate causally than more distant clinical events. An important disadvantage of surrogate end points is that if clinical outcome of interest is influenced by numerous factors (in addition to the surrogate end point), residual confounding may reduce the validity of the surrogate end point. It has been suggested that the validity of a surrogate end point is greater if it can explain at least 50% of the effect of an exposure or intervention on the outcome of interest. For instance, a biomarker may be a protein, peptide or a nucleic acid molecule.

Preferred molecular markers are markers for renal function, such as creatinine clearance, proteinuria and lipid markers, such as total cholesterol, high density lipoprotein cholesterol, low density lipoprotein cholesterol and triglycerides; inflammation markers, such as for instance C-reactive protein or markers associated with the cardiovascular and osmotic regulation, such as for instance ANP, BNP, Adrenomedullin, Endothelin-I, Vasopressin including their corresponding precursors and fragments thereof. Hereby, creatinine clearance, also termed creatinine clearance rate (CCr) is the volume of blood plasma that is cleared of creatinine per time unit. Proteinuria means the presence of an excess (i.e. more than 2 mg/ml albumin and/or creatinine) of serum proteins in the urine.

In the context of the present invention the term "normal population" refers to the healthy part of the overall population. Healthy, in this respect, are those individuals who are not in a condition by which the level of one of the markers mentioned herein is altered or affected otherwise.

In the context of the present invention the term "graft failure" refers to the rejection, breakdown or otherwise malfunctioning or of transplanted tissue, wherein the transplanted tissue is for instance surgically transplanted tissue.

In the context of the present invention expressions such as "the level of procalcitonin is not influenced anymore by the surgical trauma caused by the organ transplantation" refer to a state wherein, within the normal course of transplantation treatment, in transplant patients, typically the level of procalcitonin, which usually is elevated directly after the organ transplantation as a result of endotoxin translocation from the gut after partial ischemia/reperfusion of the gut during the surgery, is not altered due to this cause anymore.

In the context of the present invention the term "prediction" means correlating a probability of an outcome with a result obtained in the measurement of an analyte. An example of this is the measurement of a certain marker, such as procalcitonin, in a sample, the measured level of which is correlated with the probability of graft failure after organ transplant.

"Subjects" in the meaning of the invention are understood to be all persons or animals, irrespective whether or not they exhibit pathological changes, unless stated otherwise. In the meaning of the invention, any sample collected from tissues, organs, organisms or the like can be a sample of a subject to be diagnosed. In a preferred embodiment the subject according to the invention is a human.

In the context of the present invention the term "monitoring" refers to repeated determination of a subject's medical condition. Hereby, for instance the effects of a certain form of treatment on the subject's medical condition may be determined, registered, and/or documented.

In the context of the present invention the term "therapy guidance" refers to using the results of the determination of the level of a certain marker or biomarker in a subject, or the results obtained by monitoring said subject as mentioned above in order to determine the optimal course of treatment for said subject. In this way, the mode of treatment may be maintained, or may be altered or modified, depending on whether the progression the subject's medical status is as desired, or at least acceptable, or not.

In the context of the present invention expressions such as "fraction of a sample" or "extract of a sample" preferably refer to fractions obtained by methods selected from the group comprising filtration, sterile filtration, sedimentation, precipitation, centrifugation or purification by means of a purification column or membrane or similar device in order to selectively remove certain proteins, carbohydrates, lipids or other components. This may also encompass the coagulation of certain components of the sample, e.g. based on the blood coagulation cascade, and removal of the coagulated components by one of the above-mentioned methods.

In the context of the present invention the term "condition requiring antimicrobial treatment" preferably refers to a condition in which usually a medical practitioner in a technically and medically advanced society, such as in the so called first and second world states, would consider an antimicrobial treatment as being appropriate. This does not mean that such a treatment is absolutely necessary for the survival of the subject with microbial infection, but an antimicrobial treatment would at least improve the medical condition of said subject. In this context, microbial infestations with species or strains which are resistant to or otherwise unaffected by antimicrobial treatment, but for which such treatment would be desirable if it were available, are encompassed in the above mentioned conditions. A skilled person, in this case a medical practitioner, will very well be able to decide which cases are within the above specifications.

The level of PCT or fragments thereof can be obtained by any art recognized method. The level can be determined by immunoassays or other conventional techniques for determining the level of the marker. Recognized methods include sending samples of a patient's body fluid to a commercial laboratory for measurement, but also performing the measurement at the point-of-care.

The level, i.e. the concentration, of PCT in the sample of the patient may for example be attributed to the prognosis of an outcome or assessing the risk for the patient. For instance, concentrations of PCT above a certain threshold value may be indicative for a particular outcome, risk or prognosis for a patient.

The level of PCT as obtained by the methods or the use of the assays according to the present invention may be analyzed in a number of fashions well known to a person skilled in the art.

For example, each assay result obtained may be compared to a "normal" value, or a value indicating a particular prognosis, risk or outcome. A particular diagnosis/prognosis may depend upon the comparison of each assay result to such a value, which may be referred to as a diagnostic or prognostic "threshold".

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art. See, e.g., Hanley et al. 1982. *Radiology* 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group.

The skilled artisan will understand that associating a diagnostic or prognostic indicator, with a diagnosis or with a prognostic risk of a future clinical outcome is a statistical analysis. For example, a marker level of greater than X may signal that a patient is more likely to suffer from an adverse outcome than patients with a level less than or equal to X, as determined by a level of statistical significance. Additionally, a change in marker concentration from baseline levels may be reflective of patient prognosis, and the degree of change in marker level may be related to the severity of an outcome. Statistical significance is often determined by comparing two or more populations, and determining a confidence interval and/or a p value. See, e.g., Dowdy and Wearden, *Statistics for Research*, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In yet other embodiments, multiple determinations of PCT can be made, and a temporal change in the marker can be used to determine a diagnosis or prognosis. For example, a PCT level in a subject sample may be determined at an initial time, and again at a second time from a second subject sample. In such embodiments, an increase in the level from the initial time to the second time may be indicative of a particular diagnosis, or a particular prognosis. Likewise, a decrease in the level from the initial time to the second time may be indicative of a particular diagnosis, or a particular prognosis.

The term "sample" as used herein refers to a sample of bodily fluid obtained for the purpose of diagnosis, prognosis, or evaluation of a subject of interest, such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the invention the sample is selected from the group comprising a blood sample, a serum sample, a plasma sample, a cerebrospinal fluid sample, a saliva sample and a urine sample or an extract of any of the aforementioned samples. Preferably, the sample is a blood sample, most preferably a serum sample or a plasma sample.

The term "correlating" or "correlated", as used herein in reference to the use of the level of PCT or fragments thereof, refers to comparing the presence or amount of PCT or fragments thereof in a patient to its presence or amount in persons known to suffer from, or known to be at risk of, a given condition; or in persons known to be free of a given condition. As discussed above, a marker level in a patient sample can be compared to a level known to be associated with a specific prognosis. The sample's marker level is said to have been correlated with prognosis, risk and/or probability of a particular outcome; that is, the skilled artisan can use the marker level to determine the patient's prognosis, risk or probability of a particular outcome, and respond accordingly. Alternatively, the sample's marker level can be compared to a marker level known to be associated with a good outcome.

Suitable threshold levels for the stratification of subjects into different groups (categories) can be determined for each particular patient group. This can e.g. be done by grouping a reference population of patients according to their level of PCT into certain quantiles, e.g. tertiles, quartiles, quintiles or even according to suitable percentiles. For each of the quantiles or groups above and below certain percentiles, hazard ratios can be calculated comparing the risk for an adverse outcome, i.e. an "unfavourable effect", e.g. in terms of survival rate, between those patients who have received a certain medication and those who did not. In such a scenario, a hazard ratio (HR) above 1 indicates a higher risk for an adverse outcome for the patients who have received a treatment than for patients who did not.

Determining (or measuring or detecting) the level of PCT herein may be performed using a detection method and/or a diagnostic assay as explained below.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules (also termed "binders" herein) and target molecules or molecules of interest, the affinity constant is preferably greater than $10^8$ $M^{-1}$.

In the context of the present invention, "capture molecules" are molecules which may be used to bind target molecules or molecules of interest, i.e. analytes (i.e. in the context of the present invention PCT or fragments thereof having a length of at least 12 amino acids), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a RNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof, preferably a length of at least 20 amino acids.

The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

The assays can be homogenous or heterogeneous assays, competitive and non-competitive sandwich assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person. (*The Immunoassay Handbook*, Ed. David Wild, Elsevier LTD, Oxford; 3rd ed. (May 2005), ISBN-13: 978-0080445267; Hultschig C et al., Curr Opin Chem Biol. 2006 February; 10(1):4-10, PMID: 16376134), incorporated herein by reference).

In a particularly preferred embodiment the assay comprises two capture molecules, preferably antibodies which are both present as dispersions in a liquid reaction mixture, wherein a first labeling component is attached to the first capture molecule, wherein said first labeling component is part of a labeling system based on fluorescence- or chemiluminescence-quenching or amplification, and a second labeling component of said marking system is attached to the second capture molecule, so that upon binding of both capture molecules to the analyte a measurable signal is generated that allows for the detection of the formed sandwich complexes in the solution comprising the sample.

Even more preferred, said labeling system comprises rare earth cryptates or rare earth chelates in combination with a fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, auch as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrin dyes, Polymethin dyes, and the like.

In the context of the present invention, chemiluminescence based assays comprise the use of dyes, based on the physical principles described for chemiluminescent materials in Kirk-Othmer, Encyclopedia of chemical technology, 4$^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

EXAMPLES

Materials and Methods
Research Design and Subject

In this prospective cohort study all renal transplant recipients who visited the out-patient clinic between August 2001 and July 2003 and had a functioning graft for at least 1 year were eligible to participate at their next visit to the out-patient clinic. Recipients were asked to participate at a later visit to the out-patient clinic if they were ill or had signs of an infection. A total of 606 renal transplant recipients signed written informed consent from an eligible 847 (72% consent rate). The group that did not sign informed consent was comparable with the group that signed informed consent with respect to age, sex, body mass index, serum creatinine, creatinine clearance, and proteinuria. Two RTR were considered extreme outliers regarding the PCT concentration (FIG. 1) and were therefore excluded from analyses. Further details of this study have been published previously (van Ree R M, De Vries A P, Oterdoom L H et al. Abdominal obesity and smoking are important determinants of C-reactive protein in renal transplant recipients. Nephrol Dial Transplant 2005; 20(10:2524-2531). The Institutional Review Board approved the study protocol (METc 01/039) which was in adherence to the Declaration of Helsinki (Decleration of Helsinki revisited. IRB 2000; 22:10-11).

Outcome Events

All participating subjects visited the out-patient clinic at least once a year. As a secondary endpoint mortality was used. Information on mortality and graft failure is recorded by the renal transplant center and through close contact with general practitioners and referring nephrologists. Graft failure was defined as return to dialysis or re-transplantation. Graft failure and mortality of all RTR were recorded until August 2007. There was no loss to follow-up.

Renal Transplant Characteristics

Relevant transplant characteristics were taken from the Groningen Renal Transplant Database. This database holds information on all renal transplantations performed at our center since 1968, including dialysis history. Standard immunosuppressive treatment and current medication were described previously (van Ree R M, De Vries A P, Oterdoom L H et al, Abdominal obesity and smoking are important determinants of C-reactive protein in renal transplant recipients. Nephrol Dial Transplant 2005; 20(11):2524-2531). Body mass index, waist circumference, body surface area (BSA), and blood pressure were measured as described previously (van Ree R M, De Vries A P, Oterdoom L H et al. Abdominal obesity and smoking are important determinants of C-reactive protein in renal transplant recipients. Nephrol Dial Transplant 2005; 20(11):2524-2531). Smoking status and cardiovascular history were recorded with a self-report questionnaire. Cardiovascular disease history was considered positive if there was a previous myocardial infarction (MI), transient ischemic attack (TIA) or cerebrovascular accident (CVA).

Laboratory Measurements

Blood was drawn after an 8-12 h overnight fasting period. PCT analyses were performed using an immunoluminometric assay (BRAHMS PCT sensitive LIA; BRAHMS Aktiengesellschaft, Hennigsdorf, Germany) (Morgenthaler N G, Struck J, Fischer-Schulz C, Bergmann A. Sensitive immunoluminometric assay for the detection of procalcitonin. Clin Chem. 2002 May; 48(5):788-90). High sensitivity C-reactive protein (CRP) levels were determined using in-house enzyme-linked immunosorbent assays; the lowest limit of detection was 0.002 mg/l. Serum creatinine levels were determined using a modified version of the Jaffe method (MEGA AU 510, Merck Diagnostica, Darmstadt, Germany). Serum total cholesterol, HDL cholesterol, triglycerides, and urinary protein excretion were assessed as described previously 12. Proteinuria was defined as urinary protein excretion >0.5 g/24 hr.

Statistical Analysis

Analyses were performed with SPSS version 14.0 (SPSS Inc., Chicago, Ill.) and Sigma Plot version 10 (Systat software Inc., Germany). Parametric parameters are given as means±standard deviation (SD), whereas non-parametric parameters are given as median [interquartile range]. Hazard ratio's (HR) are reported with [95% confidence interval (CI)]. A two-sided P-value less than P<0.05 indicated statistical significance.

First, in order to investigate which recipients or transplanted-kidney related characteristics were associated with PCT concentrations, these factors were analysed using linear regression analyses with log PCT concentration as dependent variable. In order to determine whether PCT was correlated with CRP, creatinine clearance, or proteinuria we designed scatter-plots. Curve estimation regression statistics was used to determine the bets fit in the scatter-plots. Subsequently, independent determinants and associates of PCT were determined using backward linear regression analysis. It was adjusted for creatinine clearance and proteinuria at baseline and time between transplantation and inclusion date, in order to adjust for the fact that recipients started with a different allograft function at inclusion and for the fact that recipients were included at different time points in our study. Additional characteristics with a P-value <0.05 in the linear regression analyses were subsequently added. Retained variables were considered independent determinants and associates of PCT levels.

Sensitivity and specificity for determining graft failure or mortality were calculated by designing receiver operator characteristic (ROC) curves for PCT, CRP, proteinuria, and creatinine clearance. The optimal cutoff values were extrapolated from the curves. The area under the curve (AUC) was calculated to compare the predictive performance of PCT, CRP, proteinuria, and creatinine clearance for graft failure and PCT and CRP for mortality. Statistical differences between AUC's were compared nonparametrically by the method of DeLong et al. (DeLong E R, DeLong D M, Clarke-Pearson D L. Comparing the areas under two or more correlated receiver operating characteristic curves: a nonparametric approach. Biometrics 1988; 44(3):837-845).

Finally, time to event analyses was performed. First, PCT levels as potential predictor of graft failure and mortality using Kaplan-Meier analyses were investigated. For these analyses sex stratified tertiles of PCT were used, because the percentages of men and women were not equally divided amongst the tertiles of PCT (1st tertile: 41% women and 24% men; 2nd tertile: 31% women and 37% men; 3rd tertile: 28% women and 39% men). Secondly, univariate and multivariate Cox regression analyses were performed. PCT concentration was entered in the regression analyses as 2 log transformed variable. This means that, for example, a Hazard Ratio (HR) of 1.5 for graft failure indicates that with every doubling of the PCT concentration the HR for graft failure increases with times 1.5. It was adjusted for creatinine clearance, proteinuria, and time between transplantation and inclusion date (table 5, model 2), for recipient age and sex (table 5, model 3), and finally for dependent associates and determinants of PCT (table 5, model 4). Secondary analyses were pertained (1) with additional exclusion of RTR with CRP levels higher than 10 mg/L and (2) in nonproteinuric RTR only.

Results

A total of 575 RTR (54% male, aged 51.7±12.0 years, 84% cadaveric transplants) were analyzed. Median time between transplantation and baseline measurements was 6.1 [2.9-11.7] years. Median PCT concentration was 0.023 [0.017-0.036] ng/mL. Recipient and transplant baseline characteristics and standardized regression coefficients of the univariate linear regression analyses with log PCT concentration as independent variable are shown in table 1 and 2. With increasing levels of PCT, RTR were more often men, had greater waist circumference, and were more often smoker, had higher systolic and diastolic blood pressure, used more numbers of antihypertensive medication, had lower HDL and higher triglyceride concentration, and had higher CRP concentration. Higher levels of PCT were furthermore associated with higher donor age, higher serum creatinine concentration, lower creatinine clearance, higher proteinuria, higher frequency of acute rejection and acute rejection treatment, and higher prednisolone dose.

Figure 1:
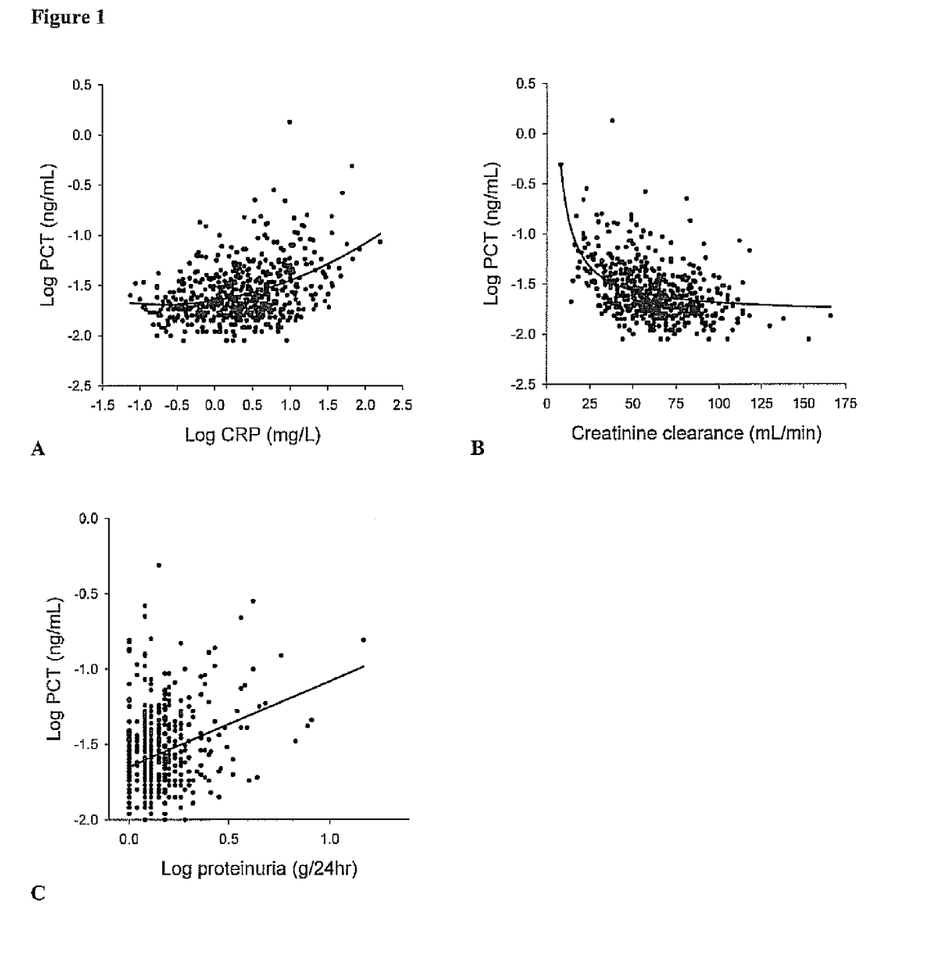
FIG. 1: Scatter-plots of Log PCT versus (a) Log CRP, (b) creatinine clearance, and (c) Log proteinuria. The association of PCT with CRP was best described by a quadratic model (Log(PCT)=−1.65+0.12*log(CRP)+0.07*(Log(CRP))2, P<0.0001). The association of PCT with creatinine clearance was best described by an inverse model (Log(PCT)=−1.80+ (11.7/creatinine clearance), P<0.0001). The association of PCT with proteinuria was best described by an linear model (Log(PCT)=−1.66+0.57*Log(proteinuria), P<0.0001)

FIG. 1 shows the correlation of PCT with (a) CRP, (b) creatinine clearance, and (c) proteinuria. Curve estimation regression analyses showed that the association of PCT with CRP was best fitted using a quadratic model that the association of PCT with creatinine clearance was best fitted using an inverse model, and that the association of PCT with proteinuria was best fitted using a linear model (see for model equations the footnote of FIG. 1, all P<0.0001). To determine the independent determinants and associates of PCT we performed a backward linear regression analysis with log PCT concentration as dependent variable and all characteristics which were significantly associated with levels of PCT in univariate analyses (see table 1 and 2). Independent determinants and associates of PCT were CRP concentration, creatinine clearance, recipient gender, proteinuria, HDL and triglyceride concentration, and donor age (table 3).

Figure 2:
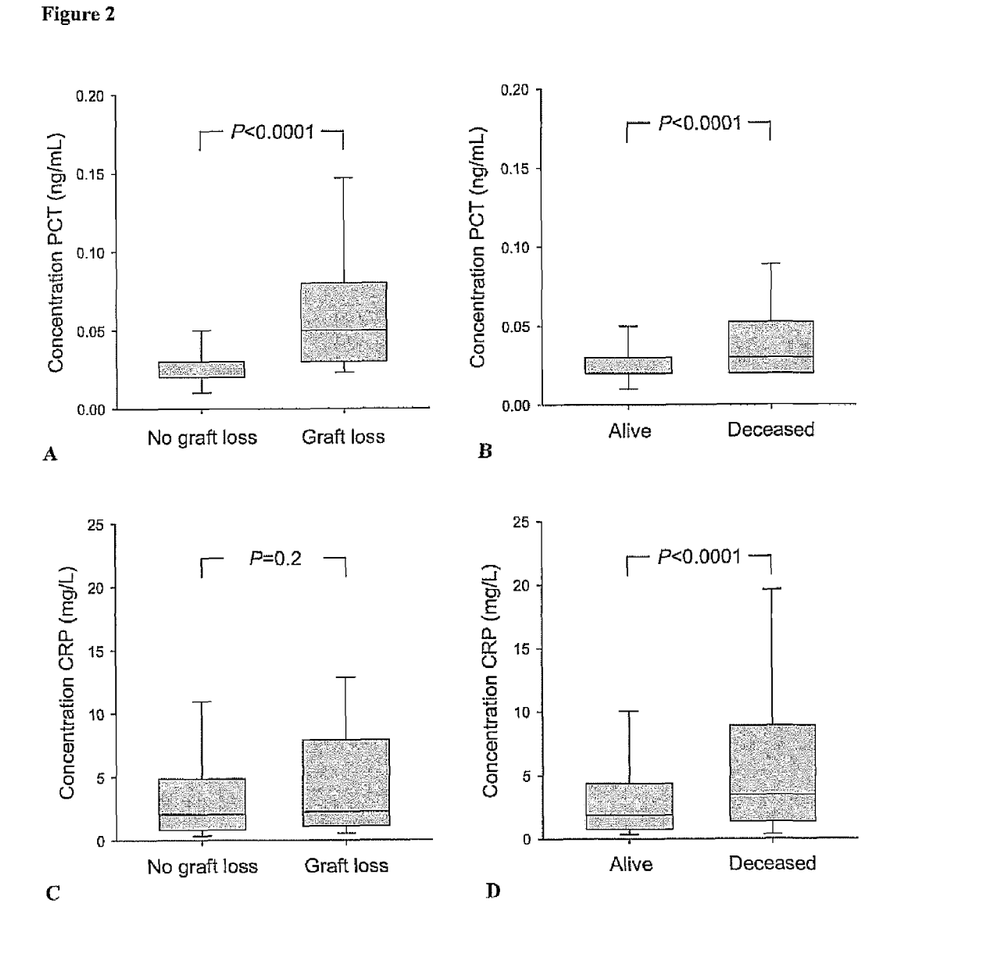
FIG. 2: Levels of PCT in (a) RTR without graft failure versus RTR with graft failure (P<0.0001) and (b) alive RTR versus deceased RTR (P<0.0001). Levels of CRP in (c) RTR without graft failure versus RTR with graft failure (P=0.2) and (d) alive RTR versus deceased RTR (P=0.0001). Differences were tested using Mann-Whitney's test.

Median follow up until graft failure was 5.2 [4.5-5.7] years and until mortality median follow up was 5.3 [4.7-5.7] years. During follow up, 41 (7%) RTR experienced graft failure and 91 (16%) RTR died. Median levels of PCT at inclusion were significantly higher in RTR who developed graft failure compared to RTR without graft failure (0.046 [0.035-0.078] ng/mL versus 0.023 [0.017-0.034] ng/mL, P<0.0001, FIG. 2a). RTR who died during follow-up had significantly higher levels of PCT at inclusion compared to RTR who did not die (0.032 [0.021-0.055] ng/mL versus 0.022 [0.017-0.034] ng/mL, P<0.0001, FIG. 2b). In comparison, CRP levels at inclusion were not significantly higher in RTR who developed graft failure compared to those who did experience graft failure (2.43 [1.18-8.04] mg/L versus 2.06 [0.81-4.87] mg/L, P=0.2, FIG. 2c). However, CRP levels in RTR who died were significantly higher compared to those who did not die (3.49 [1.38-8.91] mg/L versus 1.89 [0.74-4.38] mg/L, P=0.0001, FIG. 2d).

Figure 3:
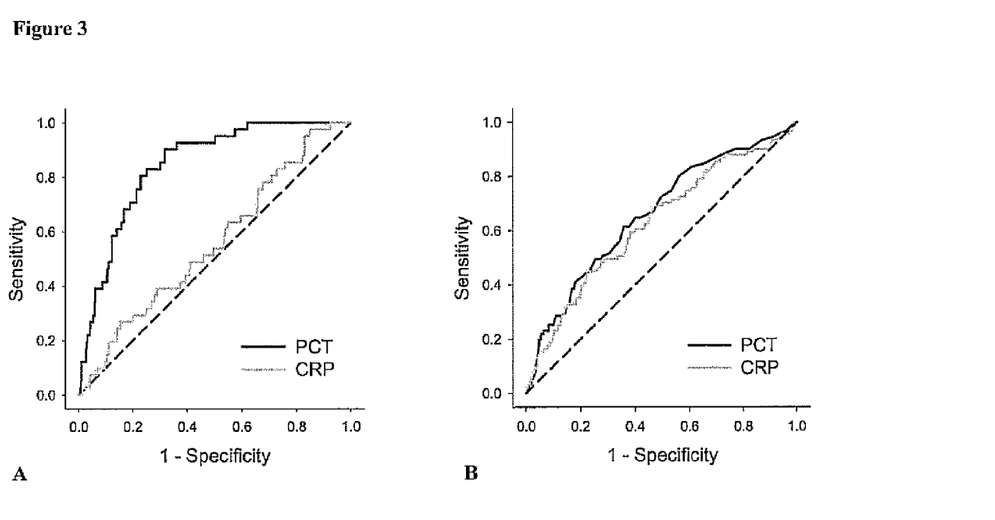
FIG. 3: ROC Curves for PCT and CRP with respect to (a) graft failure and (b) mortality. The AUC's and optimal cutoff values with corresponding sensitivity and specificity are shown in table 4.

The predictive performance of serum levels of PCT was compared with creatinine clearance, proteinuria, and CRP for graft failure and with CRP for mortality by generating ROC curves (FIGS. 3a and b, respectively). The AUC's and optimal cutoff values with corresponding sensitivity and specificity are shown in table 4. ROC analysis of the prediction of graft failure by PCT revealed a mean (SE) AUC of 0.84 (0.03). This was significantly higher compared to the AUC of CRP (0.56 (0.04), P<0.0001 compared to PCT), but equal to the AUC of creatinine clearance (0.86 (0.03), P=NS compared to PCT) and proteinuria (0.80 (0.04), P=NS compared to PCT). The optimal cutoff value to detect graft failure was 0.029 ng/mL for PCT, 51.5 mL/min for creatinine clearance, and 0.4 g/24 h for proteinuria. The optimal cutoff value to detect graft failure could not be determined for CRP because the model was not much better than random chance in predicting graft failure. ROC analysis of the prediction of mortality revealed an AUC of 0.66 (0.03) for PCT and 0.63 (0.03) for CRP (P=NS compared to each other). The optimal cutoff value to detect mortality was 0.028 ng/mL for PCT and 2.1 mg/L for CRP.

Figure 4:
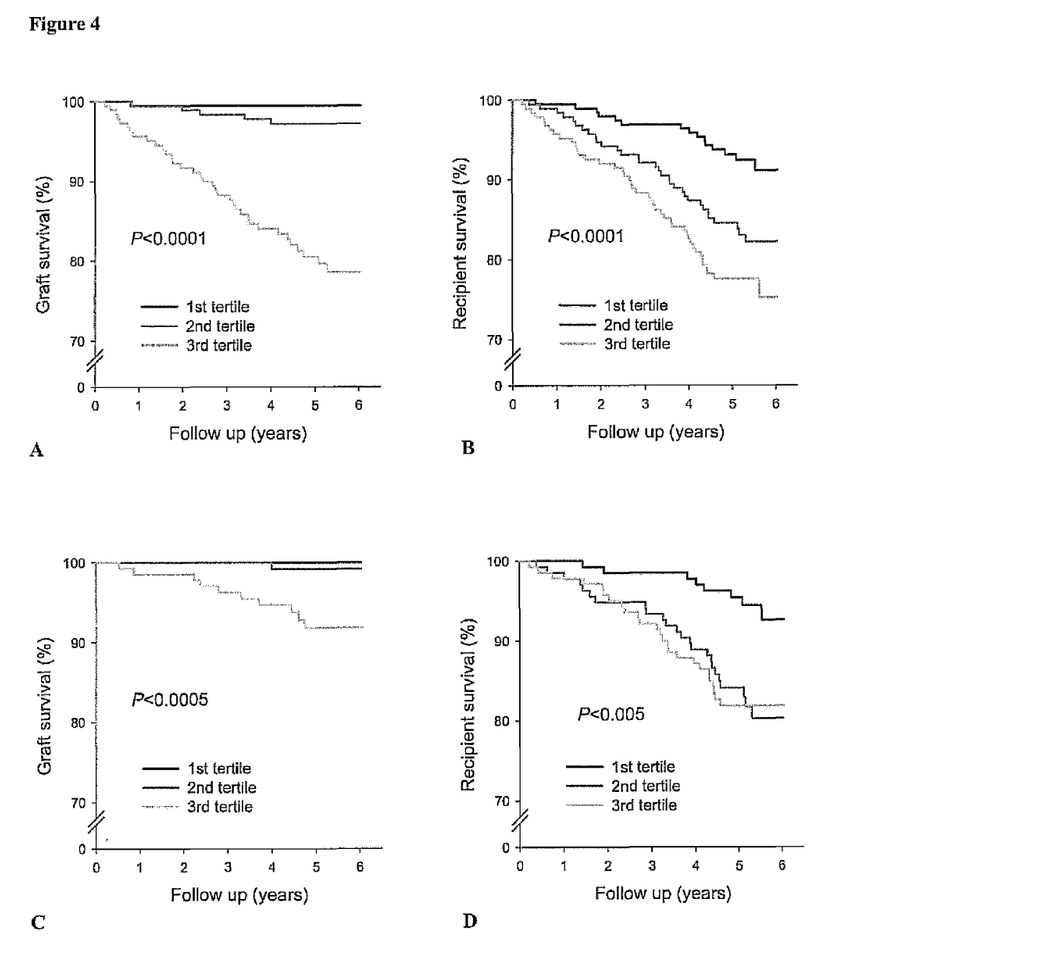
FIG. 4: Kaplan Meier curves of (a and c) graft survival and (b and d) recipient survival in sex stratified tertiles of PCT in (a and b) all RTR and (c and d) nonproteinuric RTR alone.

Finally, time to event analyses was performed. In the lowest tertile of PCT 1 (1%) RTR experienced graft failure during follow up, whereas these numbers were 5 (3%) and 35 (19%) for the middle and highest tertile, respectively (Log-Rank test: P<0.0001, FIG. 4a). Numbers for mortality were 15 (8%), 32 (17%), and 44 (23%) in increasing tertiles of PCT, respectively (Log-Rank test: P=0.0001, FIG. 4b). Table 5 shows the univariate and multivariate Cox regression analyses for late graft failure and mortality in RTR. PCT was a significant predictor for late graft failure after adjustment creatinine clearance, proteinuria, and time between transplantation and inclusion date (HR=1.7, P<0.005, table 5, model 2). The same was true with further adjustment for recipient age and sex (HR=1.6, P=0.01, table 5, model 3) and adjustment for independent associates and determinants of PCT (table 5, model 4). The significant association of PCT with mortality disappeared after adjustment for creatinine clearance, proteinuria, and time between transplantation and inclusion date (HR=1.3, P=0.06, table 5, model 2). However, significance returned after adjustment for recipient age and sex (HR=1.4, P=0.01, table 5, model 3) and maintained after adjustment for independent associates and determinants of PCT (HR=1.4, P<0.05, table 5, model 4). Results were not materially different after the exclusion of RTR with CRP levels higher than 10 mg/L or when analyses were performed in nonproteinuric RTR alone (see FIGS. 4c and d for Kaplan-Meier analysis according to stratified tertiles of PCT for nonproteinuric RTR alone).

TABLE 1

Recipient-related characteristics and univariate linear regression analyses of recipient-related characteristics and log PCT concentration.

| | | Log PCT | |
| --- | --- | --- | --- |
| | | Standardized β | P |
| Recipient demographics | | | |
| Age (years) | 51.7 ± 12.0 | 0.005 | NS |
| Male gender, n (%) | 310 (54) | 0.199 | <0.0001 |
| Body composition | | | |

TABLE 1-continued

Recipient-related characteristics and univariate linear regression analyses of recipient-related characteristics and log PCT concentration.

| | | Log PCT | |
| --- | --- | --- | --- |
| | | Standardized β | P |
| measurements | | | |
| BMI (kg/m2) | 26.1 ± 4.3 | 0.071 | NS |
| Waist circumference (cm) | 97.3 ± 13.8 | 0.197 | <0.0001 |
| Smoking, n (%) | 125 (22) | 0.085 | <0.05 |
| Blood pressure | | | |
| Systolic pressure (mmHg) | 152.9 ± 22.9 | 0.110 | <0.01 |
| Diastolic pressure (mmHg) | 89.8 ± 9.9 | 0.086 | <0.05 |
| Use of ACE-inhibitor or AII-antagonist, n | 200 (35) | 0.036 | NS |
| Use of β-blocker, n (%) | 354 (62) | −0.007 | NS |
| Number of antihypertensives | 2.0 [1.0-3.0] | 0.110 | <0.01 |
| Prior history of cardiovascular disease | | | |
| MIa, n (%) | 47 (8) | 0.021 | NS |
| TIA/CVAb, n (%) | 32 (6) | 0.006 | NS |
| Lipids | | | |
| Total cholesterol (mmol/L) | 5.6 [4.9-6.2] | −0.048 | NS |
| LDL (mmol/L) | 3.5 [2.9-4.1] | −0.076 | NS |
| HDL (mmol/L) | 1.1 [0.9-1.3] | −0.306 | <0.0001 |
| Triglycerides (mmol/L) | 1.9 [1.4-2.7] | 0.244 | <0.0001 |
| Use of statin at index, n (%) | 292 (51) | 0.002 | NS |
| Diabetes | | | |
| Glucose (mmol/L) | 4.6 [4.1-5.0] | 0.066 | NS |
| Insuline (µmol/L) | 11.1 [7.9-16.3] | 0.084 | <0.05 |
| Diabetes after transplantation, n (%) | 106 (18) | 0.020 | NS |
| Use of antidiabetic drugs (%) | 79 (14) | −0.015 | NS |
| CRP (mg/L) | 2.1 [0.8-4.9] | 0.360 | <0.0001 |

(1) TIA: Transient Ischemic Attack,
(2) CVA: Cerebrovascular Accident,
(3) Acute rejection treatment with high dose corticosteroids.
NS: not significant

TABLE 2

Transplanted kidney-related characteristics and univariate linear regression analyses of Transplanted kidney-related characteristics and log PCT concentration.

| | | Log PCT | |
| --- | --- | --- | --- |
| | | Standardized β | P |
| Donor demographics | | | |
| Age (years) | 36.9 ± 15.5 | 0.209 | <0.0001 |
| Male gender, n (%) | 316 (55) | −0.050 | NS |
| Renal allograft function | | | |
| Serum creatinine concentration (µmol/L) | 134 [112-167] | 0.537 | <0.0001 |
| CrCl (mL/min) | 61.5 ± 22.3 | −0.396 | <0.0001 |
| Proteinuria (g/24 hr) | 0.2 [0.0-0.5] | 0.082 | <0.05 |
| Proteinuria, n (%) | 164 (29) | 0.250 | <0.0001 |
| Primary renal disease, n (%) | | | |
| Primary glomerular disease | 159 (28) | | |
| Glomerulonephritis | 34 (6) | | |
| Tubular interstitial disease | 91 (16) | | |
| Polycystic renal disease | 100 (17) | −0.005 | NS |
| Dysplasia and hypoplasia | 20 (3) | | |

TABLE 2-continued

Transplanted kidney-related characteristics and univariate linear regression analyses of Transplanted kidney-related characteristics and log PCT concentration.

| | | Log PCT | |
|---|---|---|---|
| | | Standardized β | P |
| Renovascular disease | 32 (6) | | |
| Diabetes mellitus | 22 (4) | | |
| Other or unknown cause | 117 (20) | | |
| Prior dialysis modality, n (%) | | | |
| None | 47 (8) | | |
| Hemodialysis | 309 (54) | −0.021 | NS |
| Peritoneal dialysis (CAPD) | 219 (38) | | |
| Prior dialysis duration (mo) | 27 [13-48] | −0.023 | NS |
| Transplantation type, n (%) | | | |
| Postmortem donor | 481 (84) | | |
| Living donor | 76 (13) | 0.012 | NS |
| Combined transplantation | 18 (3) | | |
| Number of previous transplants, n (%) | | | |
| 0 | 515 (90) | 0.047 | NS |
| 1 or more | 60 (10) | | |
| Ischemia times | | | |
| Cold ischemia times (hr) | 22.0 [15.0-0.0] | −0.062 | NS |
| Warm ischemia times (min) | 35.0 [30.0-45.0] | −0.001 | NS |
| Delayed graft function (days of oliguria) | 0.0 [0.0-0.0] | 0.042 | NS |
| HLA mismatches, n | | | |
| HLA-AB | 1.3 ± 1.1 | 0.046 | NS |
| HLA-DR | 0.4 ± 0.6 | −0.013 | NS |
| Acute rejection, n (%) | 256 (45) | 0.091 | <0.05 |
| Acute rejection treatment, n (%) | | | |
| High doses corticosteroids | 182 (32) | 0.100 | <0.05 |
| Antilymphocyte antibodies | 74 (13) | | |
| Immunosuppresion | | | |
| Prednisolone dose, (mg/day) | 10.0 [7.5-0.0] | 0.111 | <0.01 |
| Calcineurine inhibitor, n (%) | 449 (78) | −0.08 | NS |
| Proliferation inhibitor, n (%) | | | |
| Azathioprine | 195 (34) | −0.025 | NS |
| Mycophenolate mofetil | 227 (40) | | |

NS: not significant

TABLE 3

Independent determinants and associates of PCT.

| Variable | Standardized Beta | P |
|---|---|---|
| CRP concentration | 0.30 | <0.0001 |
| Creatinine clearance | −0.30 | <0.0001 |
| Recipient gender | 0.21 | <0.0001 |
| Proteinuria | 0.16 | <0.0001 |
| HDL concentration | −0.13 | <0.001 |
| Triglyceride concentration | 0.08 | <0.05 |
| Donor age | 0.08 | <0.05 |
| R2 = 0.39 | | |

TABLE 4

AUC's and optimal cutoff values of ROC curves.

| Variable | AUC (SE) | P | Optimal cutoff value | Sensitivity (%) | Specificity (%) |
|---|---|---|---|---|---|
| Graft failure | | | | | |
| PCT (ng/mL) | 0.84 (0.03) | <0.0001 | 0.029 | 90.2 | 66.0 |
| CRP (mg/L) | 0.56 (0.04)a | 0.2 | NA | NA | NA |
| Creatinine clearance (mL/min) | 0.86 (0.03)b, c | <0.0001 | 51.5 | 85.4 | 68.7 |
| Proteinuria (g/24 hr) | 0.80 (0.04)b, c | <0.0001 | 0.4 | 80.5 | 68.7 |
| Mortality | | | | | |
| PCT (ng/mL) | 0.66 (0.03) | <0.0001 | 0.028 | 61.1 | 64.0 |
| CRP (mg/L) | 0.63 (0.03)b | 0.0001 | 2.1 | 69.2 | 53.5 | a: P < 0.0001 compared to PCT
b: not significant compared to PCT
c: P < 0.0001 compared to CRP
SE: standard error,
NA: not applicable.

TABLE 5

Univariate and multivariate Cox regression analyses for late graft failure and mortality in RTR.

| | Late graft failure | | | Mortality | | |
|---|---|---|---|---|---|---|
| | HR | 95% CI | P | HR | 95% CI | P |
| Model 1 | 3.0 | 2.3-3.9 | <0.0001 | 1.6 | 1.3-2.0 | <0.0001 |
| Model 2 | 1.7 | 1.2-2.5 | 0.003 | 1.3 | 1.0-1.6 | 0.06 |
| Model 3 | 1.6 | 1.1-2.3 | 0.01 | 1.4 | 1.1-1.9 | 0.01 |
| Model 4 | 2.0 | 1.3-3.0 | 0.002 | 1.4 | 1.0-1.9 | 0.04 |

PCT was entered in the regression analyses as 2log transformed variable and skewed data were normalized by logarithmic transformation in all analyses.
Model 1: Crude model
Model 2: Model 1 + adjustments for creatinine clearance, proteinuria, and time between transplantation and inclusion date.
Model 3: Model 2 + recipient age and sex.
Model 4: Model 3 + independent associates and determinants of PCT.

The invention claimed is:

1. A method for at least one of prediction or risk stratification for at least one of graft failure or mortality of a subject that has received an organ transplant, and monitoring and therapy guidance of such a subject, comprising
    (a) detecting and quantitating, in a sample taken from said subject, procalcitonin, wherein the level of procalcitonin is detected and quantitated with a diagnostic assay, and
    (b) comparing the result to a predetermined statistically significant cut-off value range of between 0.0127 ng/mL and 0.1 ng/mL which range is correlated with the prediction or risk stratification for at least one of graft failure or mortality in a subject that has received an organ transplant;
with the proviso that the sample is taken from the subject at least one week after transplantation;
wherein
    when the level of procalcitonin in the sample is within the cut-off value range, the subject is predicted or stratified to have an increased risk for at least one of graft failure or mortality; and
    when the level of procalcitonin in the sample is outside of the cut-off value range, the subject is predicted or stratified to not have an increased risk for at least one of graft failure or mortality; and wherein, in each case, monitoring, therapy or both are indicated in accordance with the prediction or risk stratification or both of graft failure or mortality.

2. The method of claim 1, wherein the subject has received a renal transplant.

3. The method of claim 1, wherein the subject is not suffering from a condition selected from the group consisting of: infection requiring antimicrobial therapy, sepsis, severe sepsis or septic shock.

4. The method according to claim 1, wherein the subject's level of procalcitonin is no longer influenced by the surgical trauma caused by the organ transplantation.

5. The method of claim 1, wherein said sample is selected from the group consisting of a plasma sample, a serum sample, a blood sample or fractions thereof, a lymphatic fluid sample, a urine sample, or an extract of any of said samples.

6. The method of claim 1, wherein the method is a method for prediction of long term or intermediate term graft failure.

7. The method of claim 1, wherein the method is a method for prediction of short term graft failure.

8. The method of claim 1, where the level of procalcitonin is correlated with at least one of the prediction or risk stratification for graft failure or mortality by a method selected from at least one of the following methods:
   correlation with respect to the median of the level of procalcitonin in an ensemble of pre-determined samples,
   correlation with respect to quantiles of the level of procalcitonin in an ensemble of pre-determined samples, and
   correlation with a mathematical model.

9. The method of claim 1, wherein the level of procalcitonin associated with an increased risk for graft failure and/or mortality is above the median level of the normal population.

10. The method of claim 1, wherein additionally the level of one or more further markers or clinical parameters associated with at least one of an increased risk for graft failure or mortality is determined and correlated with at least one of the prediction or risk stratification for graft failure or mortality of a subject that has received an organ transplant and monitoring and therapy guidance of such a subject.

11. The method of claim 10, wherein said one or more clinical parameters are selected from the group consisting of: age, gender, prior history of diseases, diabetes, body mass index, genetic predisposition, family history, ethnic background, and habits which affect said risk.

12. The method of claim 10, wherein said one or more further markers are selected from the group consisting of: markers for renal function, inflammation markers and markers associated with the cardiovascular and osmotic regulation.

13. The method of claim 12, wherein said marker for renal function is selected from the group consisting of creatinine clearance, proteinuria and lipid markers.

14. The method of claim 12, wherein said inflammation marker is C-reactive protein.

15. The method of claim 12, wherein said marker associated with the cardiovascular and osmotic regulation is selected from the group consisting of proBNP, proANP, proAdrenomedullin, proEndothelin, and proVasopressin.

16. The method of claim 1, wherein the diagnostic assay for procalcitonin is ultra sensitive and has a functional assay sensitivity (defined as the smallest concentration which can be determined with a maximal interassay CV of 20%) below 0.1 ng/mL.

17. The method of claim 11, wherein the habit which affect said risk is smoking, alcohol consumption or diet.

18. The method of claim 15, wherein
   the level of proBNP is detected by detecting the level of a fragment thereof selected from BNP and NT-proBNP,
   the level of proANP is detected by detecting the level of a fragment thereof selected from NT-proANP and MR-proANP,
   the level of proAdrenomedullin is detected by detecting the level of a fragment thereof selected from Adrenomedullin, PAMP and MR-proADM,
   the level of proEndothelin is detected by detecting the level of a fragment thereof selected from Endothelin-1, big-Endothelin-1, CT-proET-1 and NT-proET-1, and
   the level of proVasopressin is detected by detecting the level of a fragment thereof selected from Vasopressin, Copeptin and Neurophysin 2.

19. The method of claim 1, wherein the therapy is acute rejection treatment.

20. The method of claim 19, wherein the acute rejection treatment is selected from the group consisting of high dose corticosteroid, antilymphocyte antibodies, immunosuppression, prednisolone, calcineurine inhibitor, a proliferation inhibitor, azathioprine, and mycophenolate mofetil.

21. The method of claim 1, wherein the diagnostic assay is an immunoassay.

22. The method of claim 8, wherein the mathematical model is Cox Regression.

* * * * *